(12) United States Patent
Madabhushi et al.

(10) Patent No.: US 11,648,400 B2
(45) Date of Patent: May 16, 2023

(54) THERMOMETRIC-R2R COMBINATIONAL DAC ARCHITECTURE TO IMPROVE STIMULATION RESOLUTION

(71) Applicant: Medtronic, Inc., Minneapolis, MN (US)

(72) Inventors: Krishna Pramod Madabhushi, Chandler, AZ (US); Robert W. Hocken, Jr., Scottsdale, AZ (US)

(73) Assignee: MEDTRONIC, INC., Minneapolis, MN (US)

( * ) Notice: Subject to any disclaimer, the term of this patent is extended or adjusted under 35 U.S.C. 154(b) by 306 days.

(21) Appl. No.: 17/066,903

(22) Filed: Oct. 9, 2020

(65) Prior Publication Data

US 2022/0111209 A1    Apr. 14, 2022

(51) Int. Cl.
| | |
|---|---|
| *A61N 1/36* | (2006.01) |
| *H03M 1/68* | (2006.01) |
| *H03M 1/78* | (2006.01) |
| *A61N 1/05* | (2006.01) |

(52) U.S. Cl.
CPC ..... *A61N 1/36135* (2013.01); *A61N 1/36125* (2013.01); *H03M 1/68* (2013.01); *H03M 1/78* (2013.01); *A61N 1/0551* (2013.01)

(58) Field of Classification Search
CPC ........... H03M 1/68; H03M 1/78; H03M 7/165
See application file for complete search history.

(56) References Cited

U.S. PATENT DOCUMENTS

| | | | |
|---|---|---|---|
| 4,491,825 A | 1/1985 | Tuthill | |
| 5,959,658 A | 10/1999 | Naylor | |
| 6,181,969 B1 | 1/2001 | Gord | |
| 6,516,227 B1 | 2/2003 | Meadows et al. | |
| 8,606,362 B2 | 12/2013 | He et al. | |
| 9,056,206 B2 | 6/2015 | Torgerson et al. | |
| 9,320,899 B2 | 4/2016 | Parramon et al. | |
| 9,793,906 B1* | 10/2017 | Midha | H03L 7/083 |
| 9,987,493 B2 | 6/2018 | Torgerson et al. | |
| 10,020,817 B1 | 7/2018 | Zhang | |
| 10,340,941 B1* | 7/2019 | Nandi | H03M 1/747 |
| 10,454,487 B1 | 10/2019 | Sedighi et al. | |
| 10,848,171 B1* | 11/2020 | Carey | H03K 19/017509 |
| 10,951,227 B1* | 3/2021 | Thinakaran | H03M 1/785 |
| 11,362,668 B1* | 6/2022 | Brugger | H03M 1/747 |

(Continued)

FOREIGN PATENT DOCUMENTS

EP    1359671 A1    5/2003

OTHER PUBLICATIONS

International Search Report and Written Opinion of International Application No. PCT/US2021/071491, dated Jan. 14, 2022, 10 pp.
"Digital-Analog Converter (DAC)," retrieved from http://www.onmyphd.com/?p=digital.analog.converter on Aug. 25, 2020, 8 pp.
"Resistor Ladder," Wikipedia, the Free Encyclopedia, last edited on Apr. 11, 2020, accessed on Jun. 22, 2020, 4 pp.

(Continued)

*Primary Examiner* — Lam T Mai
(74) *Attorney, Agent, or Firm* — Shumaker & Sieffert, P.A.

(57) ABSTRACT

The disclosure describes an implementation of a combinational thermometric-R2R that includes a thermometric DAC circuit to output the coarse output steps, an R2R circuit to control the fine output steps, and a resistor in series with the thermometric and R2R circuits. The techniques of this disclosure implement a fine resolution DAC, on the order of two nanoamps per bit, that operates at low current, yet maintains monotonicity throughout the DAC output range.

18 Claims, 6 Drawing Sheets

(56) References Cited

U.S. PATENT DOCUMENTS

| | | | |
|---|---|---|---|
| 2010/0066455 A1* | 3/2010 | Kamath | H03M 1/68 341/145 |
| 2010/0102870 A1* | 4/2010 | Seedher | H03K 17/162 327/427 |
| 2013/0021181 A1* | 1/2013 | Shah | H03M 1/0692 341/110 |
| 2015/0102949 A1* | 4/2015 | Rajasekhar | H03M 1/08 341/118 |
| 2015/0200765 A1* | 7/2015 | Bonaccio | H03L 7/0814 375/374 |
| 2016/0094235 A1* | 3/2016 | Kuttner | H03M 1/662 341/144 |
| 2018/0335792 A1* | 11/2018 | Kuchipudi | G06F 1/266 |
| 2019/0222221 A1 | 7/2019 | Tanabe et al. | |
| 2019/0341926 A1* | 11/2019 | Mathur | H03M 1/361 |
| 2021/0159906 A1* | 5/2021 | Singh | H03M 3/422 |
| 2021/0159907 A1* | 5/2021 | Singh | H03M 1/1047 |

OTHER PUBLICATIONS

EDN, "Trimming a digital-to-analog converter to improve accuracy," retrieved from https://www.edn.com/trimming-a-digital-to-analog-converter-to-improve-accuracy/ on Jun. 2, 2020, published Sep. 1, 2016, 15 pp.

Kester, "Basic DAC Architectures I: String DACs and Thermometer (Fully Decoded) DACs," MT-014 Tutorial, Analog Devices, Rev. A, Oct. 2008, 6 pp.

Lim et al., "12-bit Digital-Analog Converter ECE262 Analog Circuit Design," accessed from http://people.ee.duke.edu/~jmorizio/ee299/projects_2010/12bitDAC.pdf, 2010, 49 pp. (Applicant points out, in accordance with MPEP 609.04(a), that the year of publication, 2010, is sufficiently earlier than the effective U.S. filing date, so that the particular month of publication is not in issue.).

Schweber, "Monotonicity: What are the parameters and how is it used?," Jul. 3, 2017, retrieved from https://www.analogictips.com/what-is-monotonicity-and-why-is-it-important/, 10 pp.

* cited by examiner

THERMOMETRIC-R2R COMBINATIONAL DAC ARCHITECTURE TO IMPROVE STIMULATION RESOLUTION

TECHNICAL FIELD

The disclosure relates to digital to analog converters (DACs), and specifically to R2R DACs.

BACKGROUND

A digital to analog converter (DAC) is used to convert a digital quantity (e.g., series of logic ones and zeros) to an analog output. The DAC receives a digital value, e.g. a binary number input, and outputs an analog value, e.g. a voltage or a current, that is proportional to the input digital value. The analog output maybe used in a variety of applications such as controlling relays, driving a motor, transmit communication signals, provide stimulation therapy, such as for neurostimulation and so on.

SUMMARY

In general, the disclosure describes an implementation of a combinational thermometric-R2R that includes a thermometric DAC circuit to output electrical current in coarse output steps, an R2R circuit to control the fine output steps of electrical current, and a resistor in series with the thermometric and R2R circuits. The techniques of this disclosure implement a fine resolution DAC, on the order of two nanoamps per bit, that operates at low current, yet maintains monotonicity throughout the DAC output range. The low current operation of the techniques of this disclosure may provide advantages over other types of thermometric-R2R DAC implementations, by operating at low power, which may be desirable, for example, to improve longevity in battery operated applications.

In one example, this disclosure describes a medical device comprising a digital to analog (DAC) circuit, with a thermometric digital to analog converter circuit including a first common node; an R2R digital to analog converter circuit, comprising a second common node; a first resistor, wherein: a first terminal of the first resistor connects to ground, and a second terminal of the first resistor connects to the first common node and to the second common node.

In another example, this disclosure describes a system includes an external device comprising processing circuitry; and a medical device configured to communicate with the external device, the medical device including a digital to analog (DAC) circuit comprising a thermometric digital to analog converter circuit, comprising a first common node; an R2R digital to analog converter circuit, comprising a second common node; a first resistor, wherein: a first terminal of the first resistor connects to ground, and a second terminal of the first resistor connects to the first common node and to the second common node.

In another example, this disclosure describes a circuit comprising thermometric digital to analog converter circuit including a first common node; an R2R digital to analog converter circuit, including a second common node; a first resistor, wherein: a first terminal of the first resistor connects to ground, and a second terminal of the first resistor connects to the first common node and to the second common node.

DETAILED DESCRIPTION

The combinational thermometric-R2R of this disclosure includes a thermometric DAC circuit to output the coarse output steps, an R2R circuit to control the fine output steps, and a resistor in series with the thermometric and R2R circuits. The additional resistor, as well as selection of switches, and the DAC architecture provide a practical implementation for an integrated circuit (IC) that consumes a smaller area on an IC than consumed by other DAC architecture techniques.

The techniques of this disclosure implement a fine resolution DAC, on the order of two nanoamps per bit, that operates at low current, yet maintains monotonicity throughout the DAC output range. The low current operation of the techniques of this disclosure may provide advantages over other types of thermometric-R2R DAC implementations, by operating at low power, which may be desirable, for example, to improve longevity in battery operated applications.

Figure 1:
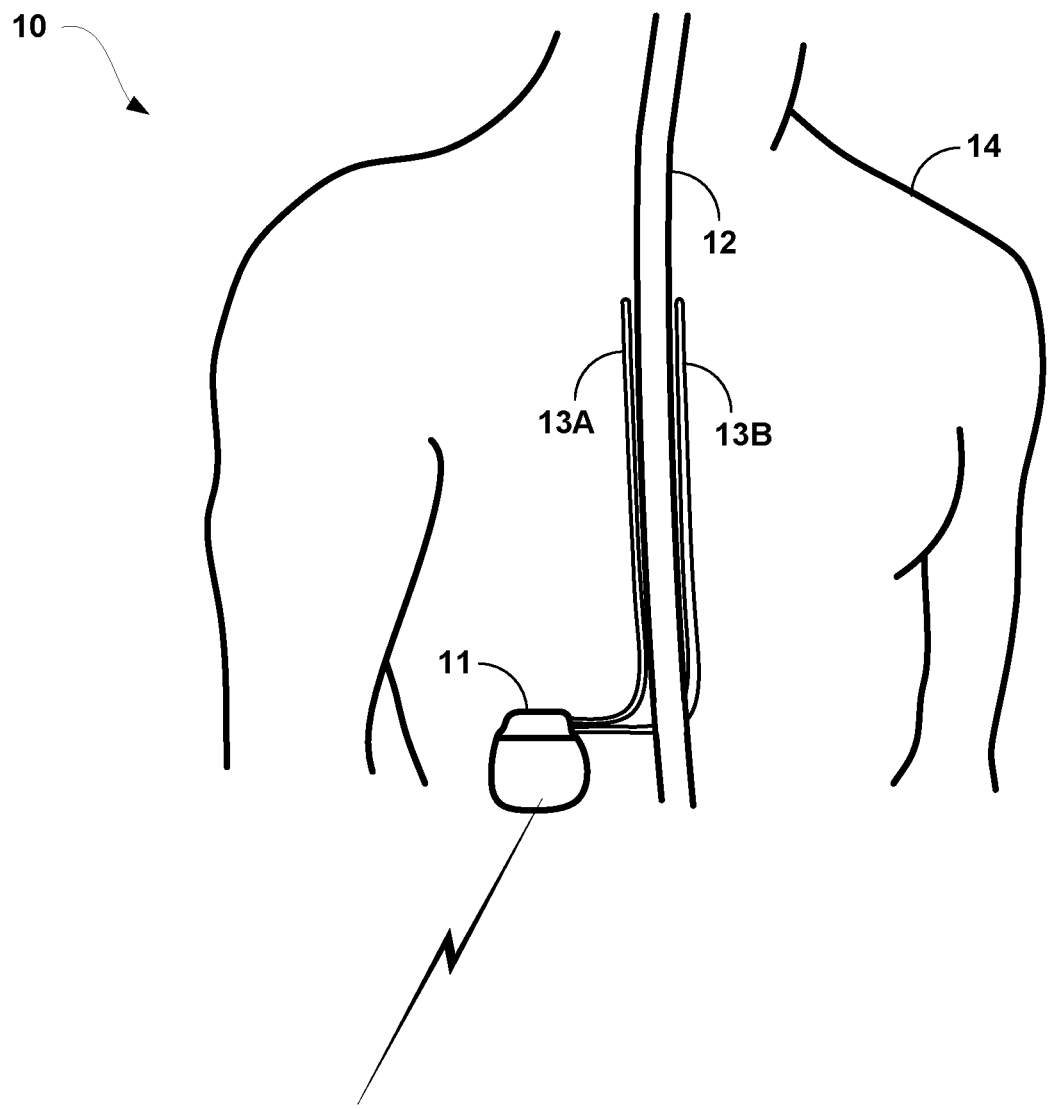
FIG. 1 is a conceptual diagram illustrating an example system that includes an implantable medical device (IMD) configured to deliver spinal cord stimulation (SCS) therapy and an external programmer, in accordance with one or more techniques of this disclosure.

FIG. 1 is a conceptual diagram illustrating an example system that includes an implantable medical device (IMD) configured to deliver spinal cord stimulation (SCS) therapy and an external programmer, in accordance with one or more techniques of this disclosure. Although the techniques described in this disclosure are generally applicable to a variety of devices including external devices and IMDs, application of such techniques to IMDs and, more particularly, implantable electrical stimulators (e.g., neurostimulators) will be described for purposes of illustration. The disclosure will refer to an implantable SCS system for purposes of illustration, but the techniques described may also apply, without limitation, to other types of devices.

As shown in FIG. 1, system 10 includes an IMD 11, leads 13A and 13B, and external programmer 15 shown in conjunction with a patient 14, who is ordinarily a human patient. In the example of FIG. 1, IMD 11 is an implantable electrical stimulator that is configured to generate and deliver electrical stimulation therapy to patient 14 via one or more electrodes of electrodes of leads 13A and/or 13B (collectively, "leads 130"), e.g., for relief of chronic pain or other symptoms. In other examples, IMD 11 may be coupled to a single lead carrying multiple electrodes or more than two leads each carrying multiple electrodes. This electrical stimulation may be delivered in the form of stimulation pulses. In some examples, IMD 11 may be configured to generate and deliver stimulation pulses to include control pulses configured to elicit ECAP signals. The control pulses may or may not contribute to therapy in some examples. In some examples, IMD 11 may, in addition to control pulses, deliver informed pulses that contribute to the therapy for the patient, but which do not elicit detectable ECAPs. IMD 11 may be a chronic electrical stimulator that remains implanted within patient 14 for weeks, months, or even years. In other examples, IMD 11 may be a temporary, or trial, stimulator used to screen or evaluate the efficacy of electrical stimulation for chronic therapy. In one example, IMD 11 is implanted within patient 14, while in another example, IMD 11 is an external device coupled to percutaneously implanted leads. In some examples, IMD 11 uses one or more leads, while in other examples, IMD 11 is leadless.

IMD 11 may be constructed of any polymer, metal, or composite material sufficient to house the components of IMD 11 (e.g., components illustrated in FIG. 2) within patient 14. In this example, IMD 11 may be constructed with a biocompatible housing, such as titanium or stainless steel, or a polymeric material such as silicone, polyurethane, or a liquid crystal polymer, and surgically implanted at a site in patient 14 near the pelvis, abdomen, or buttocks. In other examples, IMD 11 may be implanted within other suitable sites within patient 14, which may depend, for example, on the target site within patient 14 for the delivery of electrical stimulation therapy. The outer housing of IMD 11 may be configured to provide a hermetic seal for components, such as a rechargeable or non-rechargeable power source. In addition, in some examples, the outer housing of IMD 11 is selected from a material that facilitates receiving energy to charge the rechargeable power source.

Electrical stimulation energy, which may be, for example, constant current or constant voltage-based pulses may be delivered from IMD 11 to one or more target tissue sites of patient 14 via one or more electrodes (not shown) of implantable leads 130. In the example of FIG. 1, leads 130 carry electrodes that are placed adjacent to the target tissue of spinal cord 12. One or more of the electrodes may be disposed at a distal tip of a leads 130 and/or at other positions at intermediate points along the lead. Leads 130 may be implanted and coupled to IMD 11. The electrodes may transfer electrical stimulation generated by an electrical stimulation generator in IMD 11 to tissue of patient 14. In some examples the electrical stimulation generator may include a digital to analog converter circuit, such as a thermometric-R2R digital to analog converter.

Although leads 130 may each be a single lead, leads 130 may include a lead extension or other segments that may aid in implantation or positioning of leads 130. In some other examples, IMD 11 may be a leadless stimulator with one or more arrays of electrodes arranged on a housing of the stimulator rather than leads that extend from the housing. In addition, in some other examples, system 10 may include one lead or more than two leads, each coupled to IMD 11 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter of a therapy stimulation program that defines the stimulation pulses of electrical stimulation therapy by IMD 11 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, pulse shape of stimulation delivered by the electrodes. These stimulation parameters of stimulation pulses (e.g., control pulses and/or informed pulses) are typically predetermined parameter values determined prior to delivery of the stimulation pulses (e.g., set according to a stimulation program). However, in some examples, system 10 changes one or more parameter values automatically based on one or more factors or based on user input.

A test stimulation program may define stimulation parameter values that define control pulses delivered by IMD 11 through at least some of the electrodes of leads 130. These stimulation parameter values may include information identifying which electrodes have been selected for delivery of control pulses, the polarities of the selected electrodes, i.e., the electrode combination for the test stimulation program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each test stimulation program are configured to evoke a compound action potential from nerves. In some examples, the test stimulation program defines when the control pulses are to be delivered to the patient based on the frequency and/or pulse width of the informed pulses when informed pulse are also delivered. In some examples, the stimulation defined by each test stimulation program are not intended to provide or contribute to therapy for the patient. In other examples, the stimulation defined by each test stimulation program may contribute to therapy when the control pulses elicit one or both of detectable ECAP signals. In this manner, the test stimulation program may define stimulation parameters the same or similar to the stimulation parameters of therapy stimulation programs.

Although FIG. 1 is directed to SCS therapy, e.g., used to treat pain, in other examples system 10 may be configured to treat any other condition that may benefit from electrical stimulation therapy. For example, system 10 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 14.

In some examples, leads 130 includes one or more sensors configured to allow IMD 11 to monitor one or more parameters of patient 14, such as patient activity, pressure, temperature, posture, or other characteristics. The one or more sensors may be provided in addition to, or in place of, therapy delivery by leads 130.

IMD 11 is configured to deliver electrical stimulation therapy to patient 14 via selected combinations of electrodes carried by one or both of leads 130, alone or in combination with an electrode carried by or defined by an outer housing of IMD 11. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 12, such as within an intrathecal space or epidural space of spinal cord 12, or, in some examples, adjacent nerves that branch off spinal cord 12. Leads 130 may be introduced into spinal cord 12 in via any suitable region, such as the thoracic, cervical, or lumbar regions. Stimulation of spinal cord 12 may, for example, prevent pain signals from traveling through spinal cord 12 and to the brain of patient 14. Patient 14 may perceive the interruption of pain signals as a reduction in pain and, therefore, efficacious therapy results. In other examples, stimulation of spinal cord 12 may produce paresthesia which may be reduce the perception of pain by patient 14, and thus, provide efficacious therapy results.

IMD 11 generates and delivers electrical stimulation therapy to a target stimulation site within patient 14 via the electrodes of leads 130 to patient 14 according to one or more therapy stimulation programs. A therapy stimulation program defines values for one or more parameters that define an aspect of the therapy delivered by IMD 11 according to that program. For example, a therapy stimulation program that controls delivery of stimulation by IMD 11 in the form of pulses may define values for voltage or current pulse amplitude, pulse width, pulse shape, and pulse rate (e.g., pulse frequency) for stimulation pulses delivered by IMD 11 according to that program.

In some examples where relevant phases of stimulation signals cannot be detected from the types of pulses intended to be delivered to provide therapy to the patient, control pulses and informed pulses may be delivered. For example, IMD 11 is configured to deliver control stimulation in the form of control pulses to patient 14 via a combination of electrodes of leads 130, alone or in combination with an electrode carried by or defined by an outer housing of IMD 11. The tissue targeted by the control stimulation may be the same tissue targeted by the electrical stimulation therapy, delivered in the form of informed pulses. But IMD 11 may deliver control stimulation pulses via the same, at least some of the same, or different electrodes. Since control stimulation pulses are delivered in an interleaved manner with informed pulses, a clinician and/or user may select any desired electrode combination for informed pulses. Like the electrical stimulation therapy, the control stimulation may be in the form of electrical stimulation pulses or continuous waveforms.

In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. In other examples, a control stimulation pulse may include a tri-phasic pulse or pulse having more than three phases. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. In some cases, the control pulses may elicit an ECAP signal from the tissue, and IMD 11 may sense the ECAP signal via two or more electrodes on leads 130. In cases where the control stimulation pulses are applied to spinal cord 12, the signal may be sensed by IMD 11 from spinal cord 12.

IMD 11 may deliver control stimulation to a target stimulation site within patient 14 via the electrodes of leads 130 according to one or more test stimulation programs. The one or more test stimulation programs may be stored in a storage device of IMD 11. Each test program of the one or more test stimulation programs includes values for one or more parameters that define an aspect of the control stimulation delivered by IMD 11 according to each respective test program, such as current or voltage amplitude, pulse width, pulse frequency, electrode combination, and, in some examples, timing based on informed pulses to be delivered to patient 14. In some examples, IMD 11 delivers control stimulation to patient 14 according to multiple test stimulation programs.

A user, such as a clinician (not shown in FIG. 1) or patient 14, may interact with a user interface (not shown in FIG. 1) of external programmer 15 to program IMD 11. Programming of IMD 11 may refer generally to the generation and transfer of commands, programs, or other information to control the operation of IMD 11. In this manner, IMD 11 may receive the transferred commands and programs from external programmer 15 to control electrical stimulation therapy (e.g., informed pulses) and control stimulation (e.g., control pulses). For example, external programmer 15 may transmit therapy stimulation programs, test stimulation programs, stimulation parameter adjustments, therapy stimulation program selections, test program selections, user input, or other information to control the operation of IMD 11, e.g., by wireless telemetry or wired connection. As described herein, stimulation delivered to the patient may include control pulses, and, in some examples, stimulation may include control pulses and informed pulses.

In some cases, external programmer 15 may be called a physician or clinician programmer if it is primarily intended for use by a physician or clinician. In other cases, external programmer 15 may be characterized as a patient programmer if it is primarily intended for use by a patient. A patient programmer may be generally accessible to patient 14 and, in many cases, may be a portable device that may accompany patient 14 throughout the patient's daily routine. For example, a patient programmer may receive input from patient 14 when the patient wishes to terminate or change electrical stimulation therapy. In general, a physician or clinician programmer may support selection and generation of programs by a clinician for use by IMD 11, whereas a patient programmer may support adjustment and selection of such programs by a patient during ordinary use. In other examples, external programmer 15 may include, or be part of, an external charging device that recharges a power source of IMD 11. In this manner, a user may program and charge IMD 11 using one device, or multiple devices.

As described herein, information may be transmitted between external programmer 15 and IMD 11. Therefore, IMD 11 and external programmer 15 may communicate via wireless communication using any techniques known in the art. Examples of communication techniques may include, for example, radiofrequency (RF) telemetry and inductive coupling, but other techniques are also contemplated. In some examples, external programmer 15 includes a communication head that may be placed proximate to the patient's body near the IMD 11 implant site to improve the quality or security of communication between IMD 11 and external programmer 15. Communication between external programmer 15 and IMD 11 may occur during power transmission or separate from power transmission.

In some examples, IMD 11, in response to commands from external programmer 15, delivers electrical stimulation therapy according to a plurality of therapy stimulation programs to a target tissue site of the spinal cord 12 of patient 14 via electrodes (not depicted) on leads 130. In some examples, IMD 11 modifies therapy stimulation programs as therapy needs of patient 14 evolve over time. For example, the modification of the therapy stimulation programs may cause the adjustment of at least one parameter of the plurality of informed pulses. When patient 14 receives the same therapy for an extended period, the efficacy of the therapy may be reduced. In some cases, parameters of the plurality of informed pulses may be automatically updated.

Efficacy of electrical stimulation therapy may, in some cases, be indicated by one or more characteristics (e.g. an amplitude of or between one or more peaks or an area under the curve of one or more peaks) of an action potential that is evoked by a stimulation pulse delivered by IMD 11 (i.e., a characteristic of the ECAP signal). In one or more cases where stimulation pulses elicit detectable ECAPs, electrical stimulation therapy delivery by leads 130 of IMD 11 may cause neurons within the target tissue to evoke a compound action potential that travels up and down the target tissue (e.g., nerve fibers), eventually arriving at sensing electrodes of IMD 11. Furthermore, control stimulation may also elicit at least one ECAP, and ECAPs responsive to control stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse over time. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

In the example of FIG. 1, IMD 11 may perform a plurality of processing and computing functions. However, external programmer 15 instead may perform one, several, or all of these functions. In this alternative example, IMD 11 may relay sensed signals to external programmer 15 for analysis, and external programmer 15 may transmit instructions to IMD 11 to adjust the one or more parameters defining the electrical stimulation therapy based on analysis of the sensed signals. For example, IMD 11 may relay the sensed signal indicative of the sensed ECAP signal to external programmer 15.

Figure 2:
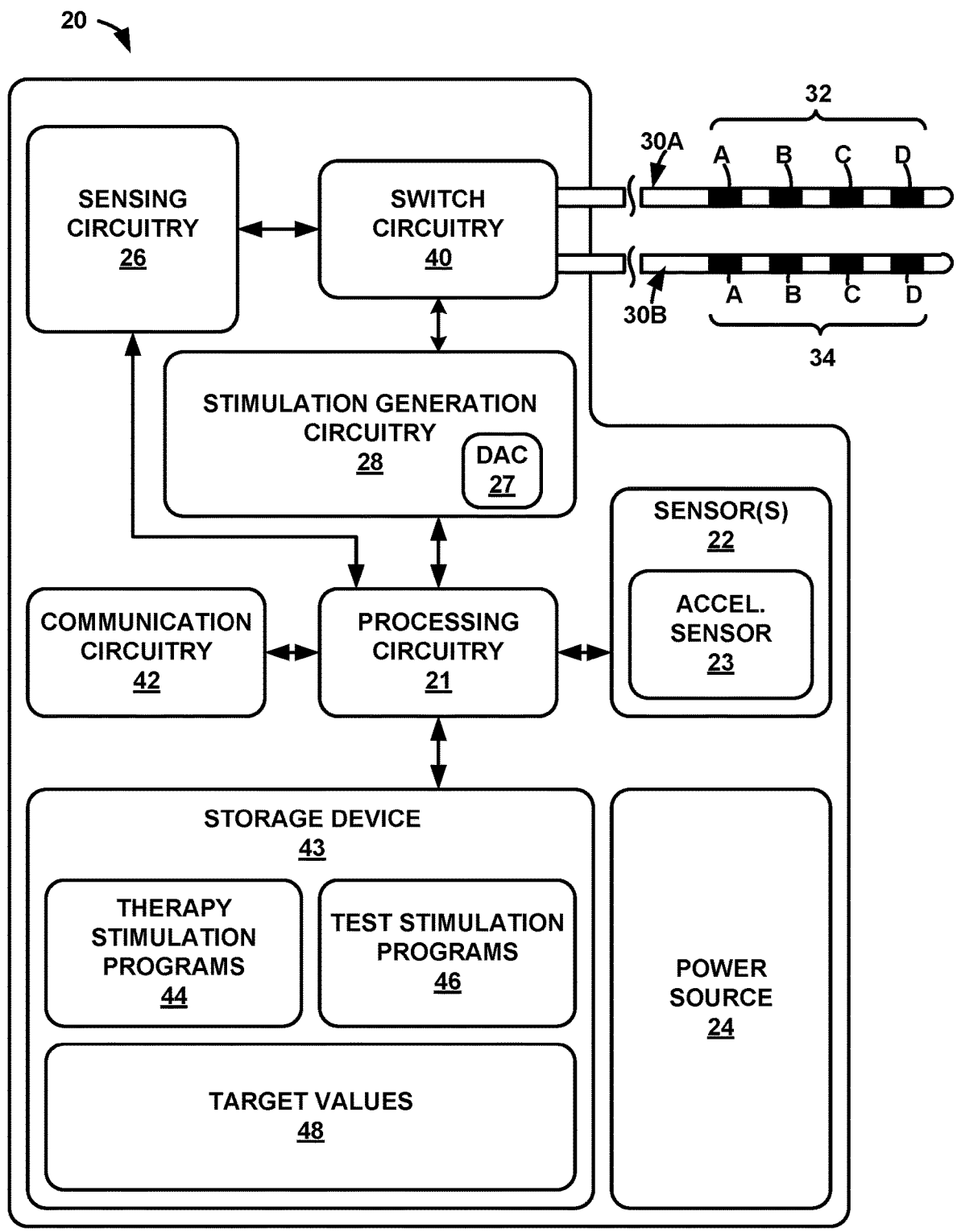
FIG. 2 is a block diagram illustrating an example configuration of components of the IMD of FIG. 1, in accordance with one or more techniques of this disclosure.

FIG. 2 is a block diagram illustrating an example configuration of components of IMD 20, in accordance with one or more techniques of this disclosure. IMD 20 may be an example of IMD 11 of FIG. 1. In the example shown in FIG. 2, IMD 20 includes stimulation generation circuitry 28, switch circuitry 40, sensing circuitry 26, Communication circuitry 42, processing circuitry 210, storage device 43, sensor(s) 22, and power source 24. As seen in FIG. 2, sensor(s) 22 include acceleration sensor 23.

In the example shown in FIG. 2, storage device 43 stores therapy stimulation programs 44 and test stimulation programs 46 in separate memories within storage device 43 or separate areas within storage device 43. Each stored therapy stimulation program of therapy stimulation programs 44 defines values for a set of electrical stimulation parameters (e.g., a stimulation parameter set), such as a stimulation electrode combination, electrode polarity, current or voltage amplitude, pulse width, pulse rate, and pulse shape. Each stored test stimulation programs 46 defines values for a set of electrical stimulation parameters (e.g., a control stimulation parameter set), such as a stimulation electrode combination, electrode polarity, current or voltage amplitude, pulse width, pulse rate, and pulse shape. Test stimulation programs 46 may also have additional information such as instructions regarding when to deliver control pulses based on the pulse width and/or frequency of the informed pulses defined in therapy stimulation programs 44. In examples in which control pulses are provided to the patient without the need for informed pulses, a separate test stimulation program may not be needed. Instead, the test stimulation program for therapy that only includes control pulses may define the same control pulses as the corresponding therapy stimulation program for those control pulses.

Accordingly, in some examples, stimulation generation circuitry 28 generates electrical stimulation signals in accordance with the electrical stimulation parameters noted above. Other ranges of stimulation parameter values may also be useful and may depend on the target stimulation site within patient 14. While stimulation pulses are described, stimulation signals may be of any form, such as continuous-time signals (e.g., sine waves) or the like. Switch circuitry 40 may include one or more switch arrays, one or more multiplexers, one or more switches (e.g., a switch matrix or other collection of switches), or other electrical circuitry configured to direct stimulation signals from stimulation generation circuitry 28 to one or more of electrodes 32, 34, or directed sensed signals from one or more of electrodes 32, 34 to sensing circuitry 26. In other examples, stimulation generation circuitry 28 and/or sensing circuitry 26 may include sensing circuitry to direct signals to and/or from one or more of electrodes 32, 34, which may or may not also include switch circuitry 40.

Sensing circuitry 26 monitors signals from any combination of electrodes 32, 34. In some examples, sensing circuitry 26 includes one or more amplifiers, filters, and analog-to-digital converters. Sensing circuitry 26 may be used to sense physiological signals, such as ECAPs. Additionally, or alternatively, sensing circuitry 26 may sense one or more stimulation pulses delivered to patient 14 via electrodes 32, 34. In some examples, sensing circuitry 26 detects electrical signals, such as stimulation signals and/or ECAPs from a particular combination of electrodes 32, 34. In some cases, the particular combination of electrodes for sensing ECAPs includes different electrodes than a set of electrodes 32, 34 used to deliver stimulation pulses. Alternatively, in other cases, the particular combination of electrodes used for sensing ECAPs includes at least one of the same electrodes as a set of electrodes used to deliver stimulation pulses to patient 14. Sensing circuitry 26 may provide signals to an analog-to-digital converter, for conversion into a digital signal for processing, analysis, storage, or output by processing circuitry 210.

Communication circuitry 42, in the example of FIG. 2, supports communication, including wireless communication, between IMD 20 and an external programmer (not shown in FIG. 2) or another computing device under the control of processing circuitry 21. Processing circuitry 21 of IMD 20 may receive, as updates to programs, values for various stimulation parameters such as amplitude and electrode combination, from the external programmer via Communication circuitry 42. Updates to the therapy stimulation programs 44 and test stimulation programs 46 may be stored within storage device 43. Communication circuitry 42 in IMD 20, as well as communication circuits in other devices and systems described herein, such as the external programmer, may accomplish communication by radiofrequency (RF) communication techniques. In addition, communication circuitry 42 may communicate with an external medical device programmer (not shown in FIG. 2) via proximal inductive interaction of IMD 20 with the external programmer. The external programmer may be one example of external programmer 15 of FIG. 1. Accordingly, communication circuitry 42 may send information to the external programmer on a continuous basis, at periodic intervals, or upon request from IMD 20 or the external programmer. In some examples, Communication circuitry 42 may also support communication between other medical devices, either implanted in, worn by or in proximity to patient 14 depicted in FIG. 1.

Processing circuitry 21 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 21 herein may be embodied as firmware, hardware, software or any combination thereof. Processing circuitry 21 controls stimulation generation circuitry 28 to generate stimulation signals according to therapy stimulation programs 44 and test stimulation programs 46 stored in storage device 43 to apply stimulation parameter values specified by one or more of programs, such as amplitude, pulse width, pulse rate, and pulse shape of each of the stimulation signals.

In the example shown in FIG. 2, the set of electrodes 32 includes electrodes 32A, 32B, 32C, and 32D, and the set of electrodes 34 includes electrodes 34A, 34B, 34C, and 34D. In other examples, a single lead may include all eight electrodes 32 and 34 along a single axial length of the lead. Processing circuitry 21 also controls stimulation generation circuitry 28 to generate and apply the stimulation signals to selected combinations of electrodes 32, 34. In some examples, stimulation generation circuitry 28 includes a switch circuit (instead of, or in addition to, switch circuitry 40) that may couple stimulation signals to selected conductors within leads 30, which, in turn, deliver the stimulation signals across selected electrodes 32, 34. Such a switch circuit may be a switch array, switch matrix, multiplexer, or any other type of switching circuit configured to selectively couple stimulation energy to selected electrodes 32, 34 and to selectively sense bioelectrical neural signals of a spinal cord of the patient (not shown in FIG. 2) with selected electrodes 32, 34.

In other examples, however, stimulation generation circuitry 28 does not include a switch circuit and switch circuitry 40 does not interface between stimulation generation circuitry 28 and electrodes 32, 34. In these examples, stimulation generation circuitry 28 includes a plurality of pairs of voltage sources, current sources, voltage sinks, or current sinks connected to each of electrodes 32, 34 such that each pair of electrodes has a unique signal circuit. In other words, in these examples, each of electrodes 32, 34 is independently controlled via its own signal circuit (e.g., via a combination of a regulated voltage source and sink or regulated current source and sink), as opposed to switching signals between electrodes 32, 34.

Electrodes 32, 34 on respective leads 30 may be constructed of a variety of different designs. For example, one or both of leads 30 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 28, e.g., via switch circuitry 40 and/or switching circuitry of the stimulation generation circuitry 28, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 30. These and other constructions may be used to create a lead with a complex electrode geometry.

In some examples, one or more of electrodes 32 and 34 are suitable for sensing stimulation signals. For instance, electrodes 32 and 34 may sense the voltage amplitude of a portion of the stimulation signals, where the sensed voltage amplitude is a characteristic of the stimulation signals. In some examples, one or more of electrodes 32 and 34 may sense a stimulation signal in response to one or more of electrodes 32 and 34 delivering a stimulation pulse to target tissue of patient 14. In some examples, the one or more of electrodes 32 and 34 which sense the stimulation signal are not the same as the one or more of electrodes 32 and 34 which deliver the stimulation pulse.

Storage device 43 may be configured to store information within IMD 20 during operation. Storage device 43 may include a computer-readable storage medium or computer-readable storage device. In some examples, storage device 43 includes one or more of a short-term memory or a long-term memory. Storage device 43 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 43 is used to store data indicative of instructions for execution by processing circuitry 21. As discussed above, storage device 43 is configured to store therapy stimulation programs 44, test stimulation programs 46, and target values 48. In some examples, processing circuitry 21 may implement the closed loop policy based on an algorithm stored at storage device 43.

Stimulation generation circuitry 28 may be configured to deliver one or more stimulation pulses, at least one of which may cause sensing circuitry 26 to sense a stimulation signal in response to the delivery of the respective pulse. In some examples, to sense a stimulation signal, sensing circuitry 26 may detect, via any one or combination of electrodes 32, 34, one or more electrical signals which are generated by stimulation generation circuitry 28 and delivered to patient 14 via any one or combination of electrodes 32, 34. In some examples, stimulation signals may include information which is useful for determining one or more parameters of upcoming therapy pulses generated by stimulation generation circuitry 28. For example, information included by a stimulation signal may include one or more characteristics which indicate an efficacy of therapy delivered to patient 14 via electrodes 32, 34. In some cases, the one or more characteristics may reflect a separation between one or more of electrodes 32, 34 and target tissue of patient 14 (e.g., spinal cord 12). Such a distance between electrodes 32, 34 and spinal cord 12 may be relevant to determining therapy since a smaller intensity (e.g., amplitude and/or pulse length) of therapy pulses is required to stimulate a nerve if electrodes 32, 34 move closer to spinal cord 12 and vice versa.

In some examples, stimulation generation circuitry 28 may generate electrical stimulation, e.g. current pulses, using a digital to analog circuitry, such as DAC 27. Processing circuitry 21 may control stimulation generation circuitry 28, to output electrical stimulation, e.g. a current pulse of a selected magnitude. DAC 27 may receive an indication of the desired magnitude for the electrical stimulation, configure one or more switches within DAC 27, and output the electrical stimulation to the patient via the one or more electrodes of IMD 20.

Determining therapy based on one or more stimulation signals may, in some cases, depend on a posture of patient 14. For example, processing circuitry 21 may be configured to determine a posture of patient 14 based on an acceleration signal generated by acceleration sensor 23. In some examples, the accelerometer signal includes a vertical component, a lateral component, and a frontal component corresponding to a vertical axis, a lateral axis, and a frontal axis, respectively. In this way, the accelerometer signal represents a three-dimensional measurement of acceleration. It may be beneficial for processing circuitry 21 to analyze one or more of the vertical axes, the lateral axis, and the frontal axis in order to determine a posture of patient 14.

In some examples, acceleration sensor 23 is configured to generate an accelerometer signal. Processing circuitry 21 is configured to identify, based on the accelerometer signal, a posture of a set of postures which patient 14 is occupying. The set of postures may include, for example, a standing posture, a sitting posture, a supine posture, a prone posture, a side-lying posture, or any combination thereof. In some examples, expected parameter values of the accelerometer signal corresponding to each posture of the set of postures are stored in storage device 43. Subsequently, processing circuitry 21 may select, based on the identified posture, a target stimulation signal value (e.g., a target range of characteristic values) for a stimulation signal sensed by IMD 20 in response to a delivery of a corresponding stimulation pulses. For example, if stimulation generation circuitry 28 generates a stimulation pulse having a stimulation amplitude and delivers the stimulation pulse to target tissue of patient 14 via one or a combination of electrodes 32, 34, processing circuitry 21 may select, based on a posture of patient 14 during the delivery of the stimulation pulse, a target range for a characteristic of the resulting stimulation signal sensed by sensing circuitry 26. Subsequently, processing circuitry 21 may determine whether to change one or more parameters of therapy stimulation programs 314 and/or test stimulation programs 46 based on whether the characteristic value is within the target range of characteristic values selected based on the posture of patient 14.

Power source 24 is configured to deliver operating power to the components of IMD 20. Power source 24 may include a battery and a power generation circuit to produce the operating power. In some examples, the battery is rechargeable to allow extended operation. In some examples, recharging is accomplished through proximal inductive interaction between an external charger and an inductive charging coil within IMD 20. Power source 24 may include any one or more of a plurality of different battery types, such as nickel cadmium batteries and lithium ion batteries.

Figure 3:
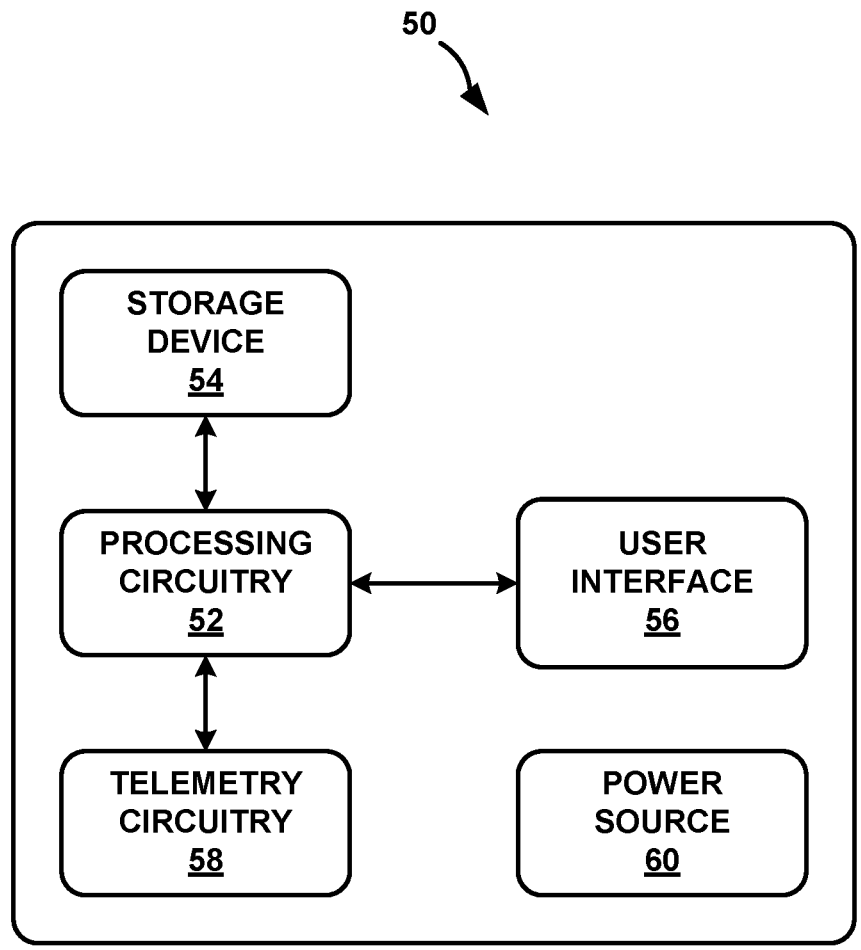
FIG. 3 is a block diagram illustrating an example configuration of components of the external programmer of FIG. 1, in accordance with one or more techniques of this disclosure.

FIG. 3 is a block diagram illustrating an example configuration of components of external programmer 50, in accordance with one or more techniques of this disclosure. External programmer 50 may be an example of external programmer 15 of FIG. 1. Although external programmer 50 may generally be described as a hand-held device, external programmer 50 may be a larger portable device or a more stationary device. In addition, in other examples, external programmer 50 may be included as part of an external charging device or include the functionality of an external charging device. As illustrated in FIG. 3, external programmer 50 may include processing circuitry 52, storage device 54, user interface 56, telemetry circuitry 58, and power source 60. Storage device 54 may store instructions that, when executed by processing circuitry 52, cause processing circuitry 52 and external programmer 50 to provide the functionality ascribed to external programmer 50 throughout this disclosure. Each of these components, circuitry, or modules, may include electrical circuitry that is configured to perform some, or all of the functionality described herein. For example, processing circuitry 52 may include processing circuitry configured to perform the processes discussed with respect to processing circuitry 52.

In general, external programmer 50 includes any arrangement of hardware, alone or in combination with software and/or firmware, configured to perform the techniques attributed to external programmer 50, and processing circuitry 52, user interface 56, and telemetry circuitry 58 of external programmer 50. In various examples, external programmer 50 may include one or more processors, such as one or more microprocessors, DSPs, ASICs, FPGAs, or any other equivalent integrated or discrete logic circuitry, as well as any combinations of such components. External programmer 50 also, in various examples, may include a storage device 54, such as RAM, ROM, PROM, EPROM, EEPROM, flash memory, a hard disk, a CD-ROM, including executable instructions for causing the one or more processors to perform the actions attributed to them. Moreover, although processing circuitry 52 and telemetry circuitry 58 are described as separate modules, in some examples, processing circuitry 52 and telemetry circuitry 58 are functionally integrated. In some examples, processing circuitry 52 and telemetry circuitry 58 correspond to individual hardware units, such as ASICs, DSPs, FPGAs, or other hardware units.

Storage device 54 (e.g., a storage device) may store instructions that, when executed by processing circuitry 52, cause processing circuitry 52 and external programmer 50 to provide the functionality ascribed to external programmer 50 throughout this disclosure. For example, storage device 54 may include instructions that cause processing circuitry 52 to obtain a parameter set from memory, select a spatial electrode movement pattern, or receive a user input and send a corresponding command to IMD 20, or instructions for any other functionality. In addition, storage device 54 may include a plurality of programs, where each program includes a parameter set that defines stimulation pulses, such as control pulses and/or informed pulses. Storage device 54 may also store data received from a medical device (e.g., IMD 11). For example, storage device 54 may store ECAP related data recorded at a sensing module of the medical device, and storage device 54 may also store data from one or more sensors of the medical device.

User interface 56 may include a button or keypad, lights, a speaker for voice commands, a display, such as a liquid crystal (LCD), light-emitting diode (LED), or organic light-emitting diode (OLED). In some examples the display includes a touch screen. User interface 56 may be configured to display any information related to the delivery of electrical stimulation, identified patient behaviors, sensed patient parameter values, patient behavior criteria, or any other such information. User interface 56 may also receive user input via user interface 56. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation. For example, the input may request an increase or decrease to stimulation intensity (e.g., amplitude, pulse width, or frequency). Programmer 50 can then transmit these requests to IMD 20. Programmer 50 may receive, and transmit, the input requesting changes to one or more parameter values during closed-loop stimulation in some examples.

Telemetry circuitry 58 may support wireless communication between the medical device and external programmer 50 under the control of processing circuitry 52. Telemetry circuitry 58 may also be configured to communicate with another computing device via wireless communication techniques, or direct communication through a wired connection. In some examples, telemetry circuitry 58 provides wireless communication via an RF or proximal inductive medium. In some examples, telemetry circuitry 58 includes an antenna, which may take on a variety of forms, such as an internal or external antenna.

Examples of local wireless communication techniques that may be employed to facilitate communication between external programmer 50 and IMD 11 include RF communication according to the 802.11 or Bluetooth® specification sets or other standard or proprietary telemetry protocols. In this manner, other external devices may be capable of communicating with external programmer 50 without needing to establish a secure wireless connection. As described herein, telemetry circuitry 58 may be configured to transmit a spatial electrode movement pattern or other stimulation parameter values to IMD 11 for delivery of electrical stimulation therapy.

In some examples, selection of stimulation parameters or therapy stimulation programs are transmitted to the medical device for delivery to a patient (e.g., patient 14 of FIG. 1).

In other examples, the therapy may include medication, activities, or other instructions that patient 14 must perform themselves or a caregiver perform for patient 14. In some examples, external programmer 50 provides visual, audible, and/or tactile notifications that indicate there are new instructions. External programmer 50 requires receiving user input acknowledging that the instructions have been completed in some examples.

According to the techniques of the disclosure, user interface 56 of external programmer 50 receives an indication from a clinician instructing a processor of the medical device to update one or more therapy stimulation programs or to update one or more test stimulation programs. Updating therapy stimulation programs and test stimulation programs may include changing one or more parameters of the stimulation pulses delivered by the medical device according to the programs, such as amplitude, pulse width, frequency, and pulse shape of the informed pulses and/or control pulses. User interface 56 may also receive instructions from the clinician commanding any electrical stimulation, including control pulses and/or informed pulses to commence or to cease.

Power source 60 is configured to deliver operating power to the components of external programmer 50. Power source 60 may include a battery and a power generation circuit to produce the operating power. In some examples, the battery is rechargeable to allow extended operation. Recharging may be accomplished by electrically coupling power source 60 to a cradle or plug that is connected to an alternating current (AC) outlet. In addition, recharging may be accomplished through proximal inductive interaction between an external charger and an inductive charging coil within external programmer 50. In other examples, traditional batteries (e.g., nickel cadmium or lithium ion batteries) may be used. In addition, external programmer 50 may be directly coupled to an alternating current outlet to operate.

Figure 4:
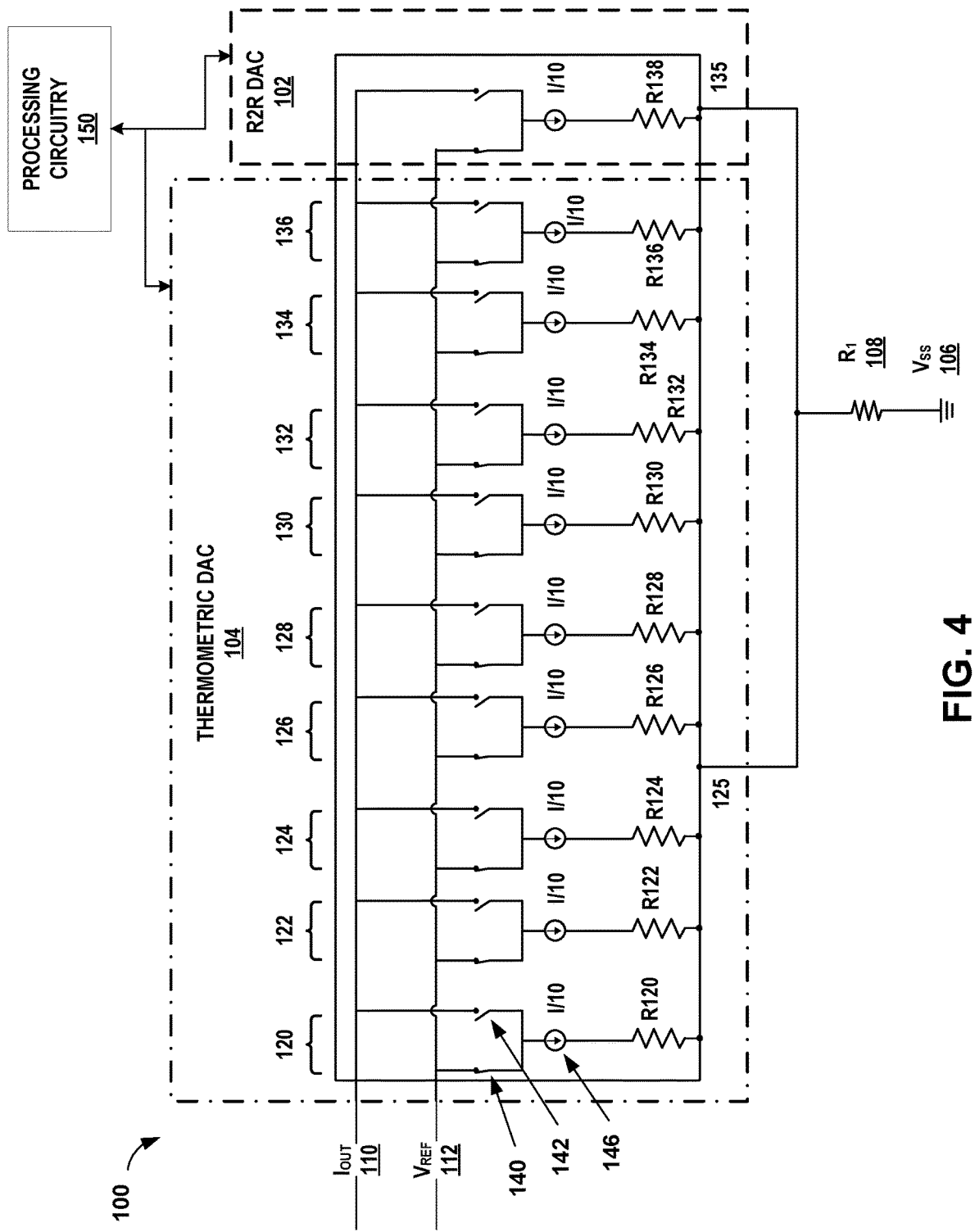
FIG. 4 is a schematic diagram illustrating an example implementation of the thermometric-R2R combinational DAC according to one or more techniques of this disclosure.

FIG. 4 is a schematic diagram illustrating an example implementation of the thermometric-R2R combinational DAC according to one or more techniques of this disclosure. DAC 100 shown in FIG. 4 is a simplified representation of the thermometric-R2R combinational DAC. There may be additional elements and/or control lines not shown to simplify the figure, and the example of FIG. 4 should not be considered limiting as to the components of example DACs described in this disclosure. DAC 100 includes thermometric DAC 104 and R2R DAC 102, which may be controlled by processing circuitry 150.

The example of thermometric DAC 104 is a 16:8 DAC with 3.32 effective number of bits (ENOB). The effective number of bits is based on the maximum phase difference induced by the analog signal output by the DAC, and the phase error for each quantization level of output electrical current. Thermometric DAC 104 includes nine channels 120-136, each with two switches, e.g. switch 140 and 142, a current supply, e.g. 146 and resistor, R120-R136. For channel 120, switch 142 connects the supply power, Iout 110 to the input of current supply 146, while switch 140 connects a reference voltage, Vref 112 to the input of power supply 146. Resistor R120 connects the output of power supply 146 to Vss 106 through resistor R1 108. Each of channels 120-136 may be configured the same as described for channel 120. Vss 106 may also be referred to as ground, signal ground, circuit ground or a reference voltage. However, in this disclosure, Vss 106 is a different reference voltage than Vref 112.

Also, the voltage at Iout 110 is a buffered voltage from Vref 112 to ensure the output voltage at Iout 110 remains approximately equal to the voltage at Vref 112. In this disclosure, approximately equal voltage means the voltage at Iout 110 is the same as the voltage at Vref 112, accounting small differences caused by tolerances in manufacturing. Iout 110 connects to a current mirror (not shown in FIG. 4) which provides the selected output current to other circuits based on the digital input to DAC 100. The total current is distributed between Iout 110 and Vref 112 based on the digital input selection. For example, when the digital input is zero, Vref supplies all the current. When the digital input is at the maximum, Iout 110 supplies all the current.

In some examples, the resistance from R120, as well as resistance from any of R120-R138, may be implemented by using two or more resistive elements in series, in parallel or in some combination of series and parallel. That is resistor R120-R138 are illustrated conceptually to indicate the resistance along respective channels 120-136. In one or more examples, resistors R120-R138 may be formed by two or more resistive elements (e.g., two or more resistors) in series, in parallel, or in some combination of series and parallel. In this disclosure, references to resistor R120-R138 should be understood as referring to the resistance along respective channels 120-136 and should not be interpreted to mean that there is only one resistor in respective channels 120-136. In some examples, active components and/or capacitors and inductors, along with or instead of resistive elements, may be utilized to provide the resistance illustrated by resistors R120-R138.

In some examples, resistor R120 may be implemented as two smaller resistive elements in series to form resistor R120. In other examples, resistor R120 may be formed by two larger value resistive elements in parallel to form resistor 120. In this manner, the resistors of DAC 100, i.e. R1 108, and resistors R120-R138, may be formed from a series, parallel, or single resistive elements that may all be of the same impedance value and all be well matched to each other. Using combinations of well-matched resistive elements may provide advantages, such as accuracy, for DAC 100. In this disclosure, "well matched" means each resistive element is of approximately equal impedance value, e.g., the same resistance value as all other resistive elements, within manufacturing tolerances. Using well matched resistors throughout DAC 100 may provide improved monotonicity when compared to other arrangements.

Each pair of switches, e.g. 140 and 142 are configured to switch with complementary timing. That is, when switch 140 is closed, switch 142 is open. Processing circuitry 150 may control the operation of each pair of switches for each channel 120-136 via control lines to each switch, such as a control line to a gate of a MOSFET (not shown in FIG. 4). In this manner, processing circuitry 150 may add or remove the contribution of each channel to the output current.

Examples of processing circuitry, such as processing circuitry 21, 52 and 150 may include any one or more of a microcontroller (MCU), e.g. a computer on a single integrated circuit containing a processor core, memory, and programmable input/output peripherals, a microprocessor (μP), e.g. a central processing unit (CPU) on a single integrated circuit (IC), a controller, a digital signal processor (DSP), an application specific integrated circuit (ASIC), a field-programmable gate array (FPGA), a system on chip (SoC) or equivalent discrete or integrated logic circuitry. A processor may be integrated circuitry, i.e., integrated processing circuitry, and that the integrated processing circuitry may be realized as fixed hardware processing circuitry, programmable processing circuitry and/or a combination of both fixed and programmable processing circuitry. Accordingly, the terms "processing circuitry," "processor" or "controller," as used herein, may refer to any one or more of the foregoing structures or any other structure operable to perform techniques described herein.

In some examples, the processing circuitry of this disclosure may be operatively coupled to a memory device. Examples of memory may include any type of computer-readable storage media, such as random access memory (RAM), read only memory (ROM), programmable read only memory (PROM), erasable programmable read only memory (EPROM), electronically erasable programmable read only memory (EEPROM), flash memory, and similar devices. In some examples the computer readable storage media may store instructions that cause processing circuitry 150 to execute the functions described herein. In some examples, the computer readable storage media may store data, such as configuration information, temporary values and other types of data used to perform the functions of this disclosure.

In operation, the digital input from processing circuitry 150 may control the operation of the switches in each of channels 120-136, and R2R DAC 102 to output the desired value of current. The output of thermometric DAC 104 is an increasing current in the form of a thermometric code, which may also be referred to as thermometer code. In thermometer code, each output is a sequence of zeros followed by a sequence of ones. Unlike binary code, there are no zeros between the ones. In some examples, processing circuitry 150 may include a converter to change a binary input to a thermometric code output to control the switches of thermometric DAC 104. Therefore, in thermometer code the lowest output is where each of channels 120-136 is off, e.g., all the current supplies, such as current supply 146, connect to Vref 112 via each respective switch, e.g. switch 142 shown in channel 120. The below sample table shows a conversion from binary code to thermometer code for a 3-bit thermometric DAC. The example of FIG. 4 has 9 output channels and may receive a 4-bit binary input. Each of channels 120-136 may carry approximately 1/10 of the output current for DAC 100. In this disclosure, "approximately" means within manufacturing and measurement tolerances. In other words, the output of each of channels 120-136 is configured to be 1/10 of the total current output by DAC 100, with some small variation in each channel caused by small differences in manufacturing.

TABLE 1

| Binary | Thermometer Code |
|---|---|
| 000 | 0000000 |
| 001 | 0000001 |
| 010 | 0000011 |
| 011 | 0000111 |
| 100 | 0001111 |
| 101 | 0011111 |
| 110 | 0111111 |
| 111 | 1111111 |

For example, in Table 1, if the input digital binary sequence is 000, then no current is output from the thermometric portion of thermometric DAC 104. If the input digital binary sequence is 001, then current from one of current sources 146 may be output. If the input digital binary sequence is 010, then current from two of current sources 146 may be output, and so forth.

R2R DAC 102 is configured to carry 1/10 of the total current output by DAC 100. In some examples, R2R DAC 102 is an 8-bit DAC and configured to output the fine resolution of output current between each step provided by thermometric DAC 104. In other words, thermometric DAC 104 is configured to provide a level change in output current, while R2R DAC 102 is configured to output current in steps between each level change.

Though R2R DAC 102 is depicted in FIG. 4 as a pair of switches and a single resistor R138 to simplify the explanation of DAC 100, R2R DAC 102 may be implemented using a plurality of resistors and switches (not shown in FIG. 4). In the example of FIG. 4, resistor R138 may represent the output impedance of R2R DAC 102.

The architecture of DAC 100 may provide several advantages over other configurations of combinational DACs. For example, the addition of resistor R1 108 between thermometric DAC 104, R2R DAC 102 and Vss 106 may reduce the resistor cell size by ten percent, when compared to other configurations. Without the addition of R1 108 the resistor cells, e.g. R120-R138 may increase by ten times in size compared to the architecture of DAC 100. In this manner, the architecture of DAC 100 may consume less area on an IC, when compared to other configurations and may therefore be more practical and lower cost to implement.

The architecture of DAC 100 may also provide approximately the same range of current output, when compared to an 8-bit DAC used alone for the same output current but provide ten times finer resolution when compared to an 8-bit DAC used alone. In addition, the architecture of DAC 100 maintains monotonicity throughout the output range of DAC 100. In other words, the output of DAC 100 increases with an increasing input and does not decrease with increasing input. Similarly, the output of DAC 100 decreases with decreasing input and does not increase with decreasing input. Mathematically, the derivative of the transfer function (binary input to analog output) never changes sign.

The architecture of DAC 100 may be implemented in a low current application, e.g. on the order of 200 nano-amps (na), where other combinational DAC architectures may be impractical. The architecture of DAC 100 means the switch sizes for the switches of each channel of thermometric DAC 104, e.g. of switches 140 and 142 may be approximately the same size and be implemented as a smaller switch, when compared to other arrangements. In some examples, a smaller switch may require less current, or voltage, to control, thereby allowing use on a low power application. In some examples, using a larger switch in a low power application may result in a switch not closing, or opening, when processing circuitry 150 sends a control signal to the switch. In contrast, the smaller switches of DAC 100 may operate reliably in a low power application, e.g. reducing the number of glitches when compared with attempting to use larger switches. Also, each R-2R block may include parasitic capacitances which may create a series of low-pass filters and affect circuit response time. Larger switches may have increased parasitics which may affect the performance of DAC 100.

In some examples, DAC 100 may be included in a medical device. The output electrical current of DAC 100 may be configured to provide electrical stimulation therapy to patient via one or more electrodes, as described above in relation to FIG. 4.

Figure 5:
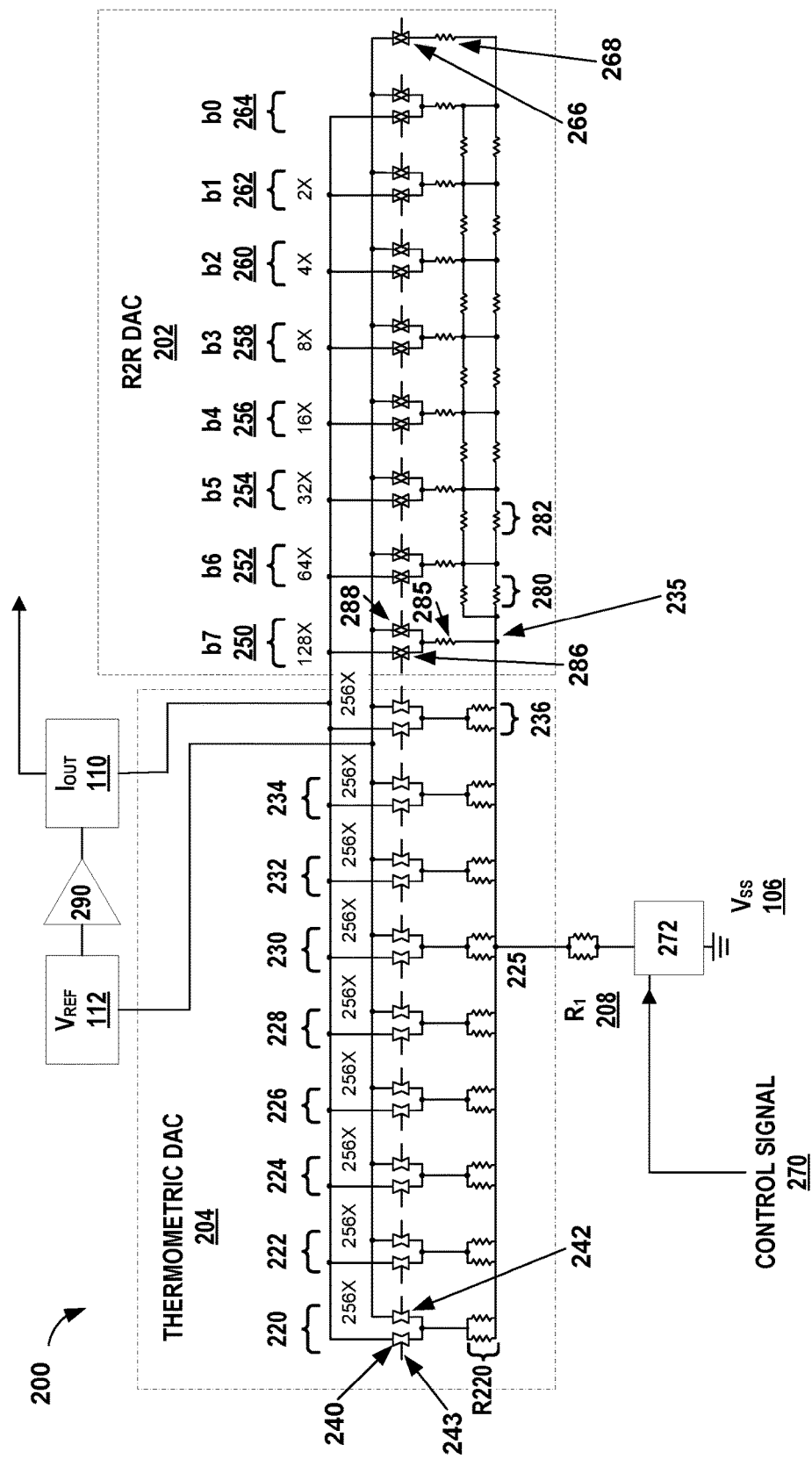
FIG. 5 is a schematic diagram illustrating an example detailed view of the thermometric-R2R combinational DAC according to one or more techniques of this disclosure.

FIG. 5 is a schematic diagram illustrating an example detailed view of the thermometric-R2R combinational DAC according to one or more techniques of this disclosure. The example of DAC 200 in FIG. 5 is an example of DAC 100 described above in relation to FIG. 4 and has similar, including same, functions and characteristics. For ease of illustration, only channel 220 of thermometric DAC 204 and b7 250 of R2R DAC 202 include reference numbers for individual components. The other channels of DAC 200 are arranged as described for channel 220 and channel 250, unless otherwise noted.

Like DAC 100 described above in relation to FIG. 4, DAC 200 includes thermometric DAC 204, R2R DAC 202, both of which connect to Vss 106 through resistor 208. In the example of FIG. 5, resistor 208 is implemented as two resistive elements in parallel. The combined effective number of bits resolution of DAC 200 is 11.322 bits. DAC 200 may receive control signals from processing circuitry, not shown in FIG. 5, which may be similar to processing circuitry 150 described above in relation to FIG. 4. Using two well matched resistive elements in parallel to create the R-2R arrangement may have advantages over using well matched resistive elements in series. In some examples, the value of the resistance may change based on the voltage across the resistance. Placing resistive elements in parallel to create the desired impedance ensures that the voltage across each resistive element is the same and therefore the impedance of each resistive element in the parallel arrangement remains matched.

As with thermometric DAC 104, thermometric DAC 204 includes nine channels 220-236, each with two switches, e.g. switch 240 and 242, and resistor, R120-R136. In the example of DAC 204, the current supply is not shown. For channel 220, switch 140 connects to supply power, Iout 110 to the input of current supply for channel 220, while switch 242 connects a reference voltage, Vref 112 to the input of the power supply for channel 220. Resistor R220 connects channel 220 to Vss 106 through resistor R1 108. Each of channels 120-136 are configured the same as described for channel 120.

Resistor R220 may be considered as being illustrated conceptually to show the resistance. Resistor R220 may be formed by one or more resistive elements (e.g., one or more physical resistors). In the example of DAC 200, resistor R220 is implemented as a pair of parallel resistive elements. The resistive elements of resistor R220 may be well matched to each other as well as to the resistive elements of R1 208. Similarly, the resistors for each of channels 222-236 are implemented as two, well matched resistive elements, which are also matched to each resistive element for each of the channels 220-236, as well as to R1 208. Implementing the resistors of each channel of thermometric DAC 204 as matched resistors may provide accurate level changes for the operation of DAC 200.

Resistor R1 208 provides an advantage for DAC 200 to perform in a low current implementation. Because the current in all the legs is constant flowing through R1 208, the constant current creates a fixed IR drop. This fixed IR drop may reduce the size requirement of the resistors in DAC 200 while maintaining the same voltage reference Vref 112. For example, without R1 208: Itotal=VREF/Rtotal, but with R1 208

$$I\text{total}=(\text{VREF}-(I\text{total}*r208))/r\text{total}$$

Where in the above equation, "R" denotes a large resistor value, "r" denotes smaller resistor value, VREF denotes the voltage at Vref 112 and r208 denotes the impedance value of R1 208. The design requirements for DAC 200 may set Itotal and Vref 112, therefore, to determine the value of "r"

$$(r\text{total}+r208)=V_{REF}/I\text{total}$$

Assuming every resistance is R, $$R\text{total}=R/10=V_{REF}/R\text{total}$$

$$(r\text{total}+r208)=R/10$$

$$(r/10+r)=R/10$$

$$r=R/11$$

In other words, by including R1 208, the value of each resistor in DAC 200 may be reduced by approximately 90% compared to DAC 200 without R1 208.

For each channel 220-236, each pair of switches, e.g. 240 and 242 are configured to switch with complementary timing. That is, when switch 240 is closed, switch 242 is open. Processing circuitry may control the operation of each pair of switches for each channel 220-236 via control lines to each switch, such as control line 243 for switch 240. In this manner, the processing circuitry may add or remove the contribution of each channel to the output current. As with thermometric DAC 104, the output of thermometric DAC 204 is an increasing current in the form of a thermometric code, or thermometer code. Each channel 220-236 of thermometric DAC 204 contributes 256X of the output electrical current. In other words, switching ON channel 236, e.g. connecting channel 236 to Iout 110 and disconnecting from Vref 112, will increase the output current by the most significant bit (MSB) of an 8-bit system. Similarly, turning ON any additional channel will also level shift the output of DAC 200 by 256× of each increment for R2R DAC 202. Said another way, for the architecture of DAC 200, each increment for each channel of thermometric DAC 204 is the same size, e.g., 256× rather than doubling on each leg, as for R2R DAC 202.

In the example of FIG. 5, R2R DAC 202 is an 8-bit DAC and configured to output the fine resolution of output current between each step provided by thermometric DAC 204. The arrangement of resistors in R2R DAC 202 may also be referred to as an R-2R resistor ladder. The contribution of each bit to the output is a simple binary weighting function of each bit. Working back from the most significant bit, e.g. b7 250 to the least significant bit (LSB), e.g. b0 264, the contribution each bit is cut in half, for example, according to the below equation:

$$Iout = \frac{I_{b7}}{2} + \frac{I_{b6}}{4} + \frac{I_{b5}}{8} + \frac{I_{b4}}{16} + \frac{I_{b3}}{32} + \frac{I_{b2}}{62} + \frac{I_{b1}}{128} + \frac{I_{b0}}{256}$$

For the most significant bit, b7 250, switch 286 connects to Iout 110, while switch 188 connects to Vref 112. As with thermometric DAC 204, each of the two switches for each bit, or channel b7 250-b0 264 are configured to switch with complementary timing. Therefore, when switch 286 is closed and connects resistor 285 to Iout 110, then switch 288 is open, disconnecting resistor 285 from Vref 112, and vice versa. Each switch of each of bits b7 250-b0 264, e.g. switch 286 and switch 288, may be controlled by a control line from processing circuitry (not shown in FIG. 5).

In the example of R2R DAC 202, the value of resistor 285 is the same as the value for each resistor of parallel resistors 280, e.g., 2R ohms. Therefore, the magnitude of resistance between each bit b7 250-b0 264 is R ohms, thus forming an R-2R network.

The architecture of R2R DAC 202 means that the output impedance of the R-2R resistor network is always equal to the value of the parallel combination of resistors 280, resistors 282 and so on for R2R DAC channels 250-264, regardless of the size (number of bits) of R2R DAC 202. In other words, in an example in which R2R DAC 202 is implemented as a 4-bit DAC, the output impedance would still remain equal to value of the parallel combination of resistors 280.

R2R DAC 202 also includes switch 266 and resistor 268. In the example of FIG. 5, buffer 290 may be implemented using a bipolar junction transistor (BJT) configuration. Switch 266 and resistor 268 provide a current bias to start up the circuitry of DAC 200. In other examples, such as implementing buffer 290 using other circuitry, e.g. a MOSFET differential pair, DAC 200 may not include the bias circuitry of switch 266 and resistor 268.

As described above in relation to FIG. 4, the architecture of DAC 200 means the switch sizes for the switches of each channel of thermometric DAC 204, e.g. of switches 240 and 242 may be approximately the same size and be implemented as a smaller switch, when compared to other arrangements. Similarly, the switch sizes for each channel of R2R DAC 202 may be approximately the same size, though the contribution to the output current for DAC 202 is divided, as described above. In this disclosure, switch size may refer to current carrying capacity, switch length, width, switch area, channel size and so on.

In some examples, DAC 200 may also include an enable switch 272, which may connect R1 208 to Vss 106. To disable the operation of DAC 200, control signal 270 may cause enable switch 272 to open and disconnect DAC 200 from Vss 106. In some examples, control signal 270 may be a signal from processing circuitry, such as processing circuitry 150 described above in relation to FIG. 4.

Figure 6:
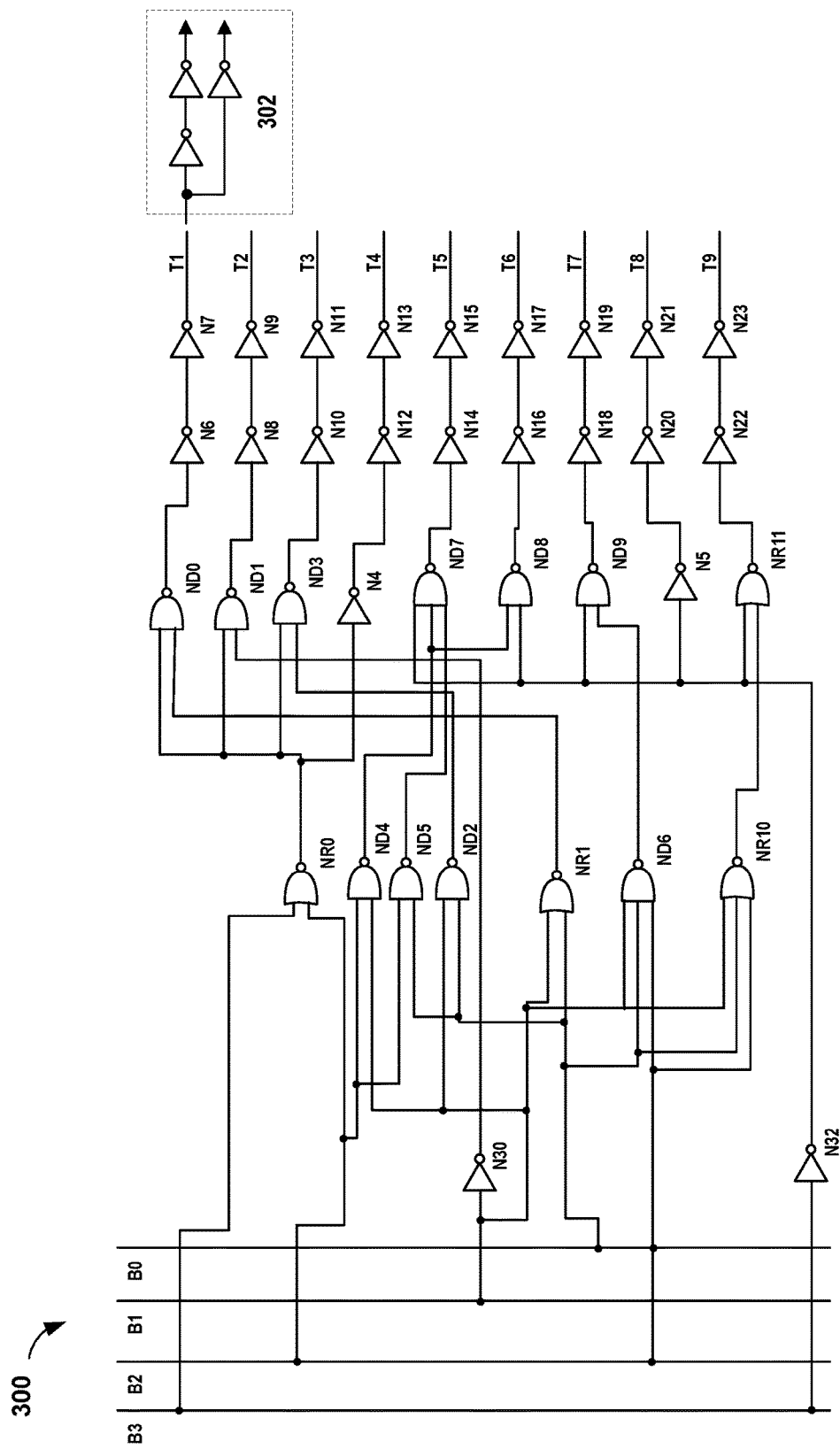
FIG. 6 is a schematic diagram illustrating an example of a digital to thermometric code converter implemented using logic gates, according to one or more techniques of this disclosure.

FIG. 6. is a schematic diagram illustrating an example of a binary to thermometric code converter implemented using logic gates, according to one or more techniques of this disclosure. Circuit 300 in the example of FIG. 6 is just one example implementation of a binary to thermometric code, or thermometer code, converter. Other techniques may include a different logic circuit layout, another type of circuit, a conversion using processing circuitry executing instructions from computer readable storage medium, an application specific integrated circuit and other similar techniques.

Circuit 300 receives an input 4-bit binary word at input terminals B0-B3 and outputs a corresponding thermometric code equivalent from output terminals T1-T9. Output terminals T1-T9 may connect to control terminals for the switches of thermometric DAC 104 and 204, e.g. control line 243 described above in relation to FIG. 5. In some examples, each of output terminals T1-T9 may connect to a complementary circuit, similar to circuit 302. For example, the single output for T1 may connect to the single input terminal for circuit 302. Each of the two outputs from circuit 302 may connect to a switch pair. For example, a first output from circuit 302 may connect to the control terminal 243 for switch 240, while the second output may connect to the control terminal for switch 242. In this manner when T1 outputs either a logical 1 or a logical zero, each of switches 240 and 242 are configured to switch with complementary timing. The other outputs T2-T9 may connect to a respective channel of thermometric DAC 104 or 204 in a similar manner.

Input terminal B3 connects to a first input of NOR gate NR0 and to an input for inverter N32. Input terminal B2 connects to the second input of NOR gate NR0 and to one of three inputs for NAND gate ND10. The output of NOR gate NR0 connects to inverter N4 as well as to an input for NAND gates ND0, ND1 and ND3. The output of N32 connects to one of three inputs for NAND gate ND7 as well as to inputs for NAND gates ND8, ND8, and NOR gate NR11. Input terminal B1 connects to the input of inverter N30, inputs for NAND gates ND4 and ND2 and to inputs for NOR GATES NR1 and NR10. Input terminal B0 connects to the input of NAND gates ND5, ND2, and ND6 as well as NOR gates NR1, and NR10.

The output of ND4 connects to an input of NAND gates ND7 and ND8. The output of ND5 connects to an input of ND7. The output of ND2 connects to an input of NAND gate ND3. The output of NR1 connects to an input of NAND gate ND0. The output of ND6 connects to an input of NAND gate ND9. The output of NR10 connects to an input of NOR gate NR11.

The output of ND0 connects to output T1 through inverters N6 and N7. The output of ND1 connects to output T2 through inverters N8 and N9. The output of ND3 connects to output T3 through inverters N10 and N11. The output of ND3 connects to output T4 through inverters N12 and N13. The output of N4 connects to output T5 through inverters N14 and N15. The output of ND8 connects to output T6 through inverters N16 and N17. The output of ND9 connects to output T7 through inverters N18 and N19. The output of N5 connects to output T8 through inverters N20 and N21. The output of NR11 connects to output T9 through inverters N22 and N23.

The techniques of this disclosure may also be described in the following examples.

Example 1: A medical device comprising a digital to analog (DAC) circuit includes a thermometric digital to analog converter circuit, comprising a first common node; an R2R digital to analog converter circuit, comprising a second common node; a first resistor, wherein: a first terminal of the first resistor connects to ground, and a second terminal of the first resistor connects to the first common node and to the second common node.

Example 2: The medical device of example 1, wherein the first resistor has a first impedance value; wherein the thermometric digital to analog converter circuit further comprises a plurality of channels, wherein each respective channel of the plurality of channels comprises respective one or more resistors connected to the first common node, wherein a resistance, for the respective one or more resistors, of the plurality of channels has an impedance value that is approximately equal to the first impedance value.

Example 3: The medical device of any combination of examples 1-2, wherein each respective one or more resistors of the plurality of channels comprises two parallel resistive elements.

Example 4: The medical device of any combination of examples 1-3, wherein the R2R digital to analog converter circuit comprises an output impedance connected to the second common node, and wherein the output impedance is approximately equal to the first impedance value.

Example 5: The medical device of any combination of examples 1-4, wherein the thermometric digital to analog converter circuit further comprises a plurality of channels, wherein each respective channel of the plurality of channels comprises a respective pair of switches including a first switch and a second switch, wherein a size of the first switch is approximately equal to a size of the second switch, wherein a size of the first switch for a first channel of the plurality of channels is approximately equal to the size of the first switch for each respective channel of the plurality of channels.

Example 6: The medical device of any combination of examples 1-5, wherein the first switch is configured to be open when the second switch is closed, and wherein the first switch is configured to be closed when the second switch is open.

Example 7: The medical device of any combination of examples 1-6, wherein the first switch is configured to connect to a supply voltage and the second switch is configured to connect to a reference voltage.

Example 8: The medical device of any combination of examples 1-7, further comprising processing circuitry configured to control the operation of the plurality of channels, wherein the processing circuitry is configured to add or remove a contribution of each channel to an output electrical current of the circuit.

Example 9: The medical device of any combination of examples 1-8, wherein the output electrical current is configured to provide electrical stimulation therapy to a patient via one or more electrodes.

Example 10: A system includes an external device comprising processing circuitry; and a medical device configured to communicate with the external device, the medical device including a digital to analog (DAC) circuit includes a thermometric digital to analog converter circuit, comprising a first common node; an R2R digital to analog converter circuit, comprising a second common node; a first resistor, wherein: a first terminal of the first resistor connects to ground, and a second terminal of the first resistor connects to the first common node and to the second common node.

Example 11: The system of example 10, wherein the first resistor has a first impedance value; wherein the thermometric digital to analog converter circuit further comprises a plurality of channels, wherein each respective channel of the plurality of channels comprises respective one or more resistors connected to the first common node, wherein a resistance, for the respective one or more resistors, of the plurality of channels has an impedance value that is approximately equal to the first impedance value.

Example 12: The system of any combination of examples 10-11, wherein each respective one or more resistors of the plurality of channels comprises two parallel resistive elements.

Example 13: The system of any combination of examples 10-12, wherein the R2R digital to analog converter circuit comprises an output impedance connected to the second common node, and wherein the output impedance is approximately equal to the first impedance value.

Example 14: The system of any combination of examples 10-13, wherein the thermometric digital to analog converter circuit further comprises a plurality of channels, wherein each respective channel of the plurality of channels comprises a respective pair of switches including a first switch and a second switch, wherein a size of the first switch is approximately equal to a size of the second switch, wherein a size of the first switch for a first channel of the plurality of channels is approximately equal to the size of the first switch for each respective channel of the plurality of channels.

Example 15: The system of any combination of examples 10-14, wherein the first switch is configured to be open when the second switch is closed, and wherein the first switch is configured to be closed when the second switch is open.

Example 16: The system of any combination of examples 10-15, wherein the first switch is configured to connect to a supply voltage and the second switch is configured to connect to a reference voltage.

Example 17: The system of any combination of examples 10-16, further comprising processing circuitry configured to control the operation of the plurality of channels, wherein the processing circuitry is configured to add or remove a contribution of each channel to an output electrical current of the circuit.

Example 18: The system of any combination of examples 10-17, wherein the output electrical current is configured to provide electrical stimulation therapy to a patient via one or more electrodes.

Example 19: A circuit includes thermometric digital to analog converter circuit including a first common node; an R2R digital to analog converter circuit, including a second common node; a first resistor, wherein: a first terminal of the first resistor connects to ground, and a second terminal of the first resistor connects to the first common node and to the second common node.

Example 20: The circuit of example 19, wherein the first resistor has a first impedance value; wherein the thermometric digital to analog converter circuit further comprises a plurality of channels, wherein each respective channel of the plurality of channels comprises respective one or more resistors connected to the first common node, wherein a resistance, for the respective one or more resistors, of the plurality of channels has an impedance value that is approximately equal to the first impedance value, and wherein each respective one or more resistors of the plurality of channels comprises two parallel resistive elements.

Various examples of the disclosure have been described. These and other examples are within the scope of the following claims.

What is claimed is:

1. A medical device comprising a digital to analog (DAC) circuit, the circuit comprising:
    a thermometric digital to analog converter circuit, comprising a first common node;
    an R2R digital to analog converter circuit, comprising a second common node;
    a first resistor, wherein:
        the first resistor has a first impedance value,
        a first terminal of the first resistor connects to ground, and
        a second terminal of the first resistor connects to the first common node and to the second common node;
    wherein the thermometric digital to analog converter circuit further comprises a plurality of channels,
    wherein each respective channel of the plurality of channels comprises respective one or more resistors connected to the first common node,
    wherein a value of the one or more resistors is approximately equal to the first impedance value.

2. The medical device of claim 1, wherein each respective one or more resistors of the plurality of channels comprises two parallel resistive elements.

3. The medical device of claim 1,
    wherein the R2R digital to analog converter circuit comprises an output impedance connected to the second common node, and
    wherein the output impedance is approximately equal to the first impedance value.

4. The medical device of claim 1,
    wherein the thermometric digital to analog converter circuit further comprises a plurality of channels,
    wherein each respective channel of the plurality of channels comprises a respective pair of switches including a first switch and a second switch,
    wherein a size of the first switch is approximately equal to a size of the second switch,
    wherein a size of the first switch for a first channel of the plurality of channels is approximately equal to the size of the first switch for each respective channel of the plurality of channels.

5. The medical device of claim 4,
    wherein the first switch is configured to be open when the second switch is closed, and
    wherein the first switch is configured to be closed when the second switch is open.

6. The medical device of claim 5, wherein the first switch is configured to connect to a supply voltage and the second switch is configured to connect to a reference voltage.

7. The medical device of claim 4, further comprising processing circuitry configured to control operation of the plurality of channels, wherein the processing circuitry is configured to add or remove a contribution of each channel to an output electrical current of the circuit.

8. The medical device of claim 7, wherein the output electrical current is configured to provide electrical stimulation therapy to a patient via one or more electrodes.

9. A system comprising:
    an external device comprising processing circuitry; and
    a medical device configured to communicate with the external device, the medical device including a digital to analog (DAC) circuit, the circuit comprising:
        a thermometric digital to analog converter circuit, comprising a first common node;
        an R2R digital to analog converter circuit, comprising a second common node;
        a first resistor, wherein:
            the first resistor has a first impedance value,
            a first terminal of the first resistor connects to ground, and
            a second terminal of the first resistor connects to the first common node and to the second common node.
    wherein the thermometric digital to analog converter circuit further comprises a plurality of channels,
    wherein each respective channel of the plurality of channels comprises respective one or more resistors connected to the first common node,
    wherein a value of the one or more resistors is approximately equal to the first impedance value.

10. . The system of claim 9, wherein each respective one or more resistors of the plurality of channels comprises two parallel resistive elements.

11. The system of claim 9, wherein the R2R digital to analog converter circuit comprises an output impedance connected to the second common node, and wherein the output impedance is approximately equal to the first impedance value.

12. The system of claim 9,
    wherein the thermometric digital to analog converter circuit further comprises a plurality of channels,
    wherein each respective channel of the plurality of channels comprises a respective pair of switches including a first switch and a second switch,
    wherein a size of the first switch is approximately equal to a size of the second switch, wherein a size of the first switch for a first channel of the plurality of channels is approximately equal to the size of the first switch for each respective channel of the plurality of channels.

13. The system of claim 12,
wherein the first switch is configured to be open when the second switch is closed, and
wherein the first switch is configured to be closed when the second switch is open.

14. The system of claim 13, wherein the first switch is configured to connect to a supply voltage and the second switch is configured to connect to a reference voltage.

15. The system of claim 12, further comprising processing circuitry configured to control operation of the plurality of channels, wherein the processing circuitry is configured to add or remove a contribution of each channel to an output electrical current of the circuit.

16. The system of claim 15, wherein the output electrical current is configured to provide electrical stimulation therapy to a patient via one or more electrodes.

17. A circuit comprising:
thermometric digital to analog converter circuit including a first common node;
an R2R digital to analog converter circuit, including a second common node;
a first resistor, wherein:
the first resistor has a first impedance value,
a first terminal of the first resistor connects to ground, and
a second terminal of the first resistor connects to the first common node and to the second common node
wherein the thermometric digital to analog converter circuit further comprises a plurality of channels,
wherein each respective channel of the plurality of channels comprises respective one or more resistors connected to the first common node,
wherein a value of the one or more resistors is approximately equal to the first impedance value, and
wherein each respective one or more resistors of the plurality of channels comprises two parallel resistive elements.

18. The circuit of claim 17,
wherein each respective one or more resistors of the plurality of channels comprises two parallel resistive elements.

* * * * *